United States Patent [19]
Johal

[11] Patent Number: 4,588,691
[45] Date of Patent: May 13, 1986

[54] METHOD FOR PREPARATION OF FRACTION I PROTEIN AND BY-PRODUCTS THEREOF

[76] Inventor: Sarjit S. Johal, 935 Canyon View Dr. #302, Sagamore Hills, Ohio 44067

[21] Appl. No.: 584,669

[22] Filed: Feb. 29, 1984

[51] Int. Cl.$^4$ .................. C12N 9/88; A61K 35/78; C08G 8/02

[52] U.S. Cl. .................. 530/379; 260/112 R; 536/128; 424/195.1; 530/379; 435/816

[58] Field of Search .................. 435/232, 68, 100, 101, 435/102, 103, 104, 105, 816; 424/195; 47/58; 536/127, 128; 260/112 R

[56] References Cited

U.S. PATENT DOCUMENTS

| | | | |
|---|---|---|---|
| 3,382,229 | 5/1968 | Patton et al. | 536/127 |
| 4,119,435 | 10/1978 | Nakao et al. | 127/34 |
| 4,268,632 | 5/1981 | Wildman et al. | 435/232 |
| 4,340,676 | 7/1982 | Bourque | 435/232 |
| 4,347,324 | 8/1982 | Wildman et al. | 435/232 |
| 4,400,471 | 8/1983 | Johal | 435/232 |

OTHER PUBLICATIONS

The Merck Index, published by Merck & Co. Inc., 1976.
Sarjit Johal and Don P. Bourque (1979) Science 204:75–77 "Crystalline Ribulose 1,5-Bisphosphate Carboxylase . . . from Spinach".
Janet Paulsen and M. D. Lane (1966) Biochem. 5:2350–2357 "Spinach Ribulose Diphosphate Carboxylase . . . of the Enzyme".

*Primary Examiner*—Thomas G. Wiseman
*Assistant Examiner*—Robin Lyn Teskin
*Attorney, Agent, or Firm*—Townsend & Townsend

[57] ABSTRACT

An improved method for the purification of ribulose, 1,5-bisphosphate carboxylase (RuBisCO) comprises comminuting and homogenizing a plant material, such as leaves, in an aqueous solution. After fractionation to release the RuBisCO, sufficient polyethylene glycol (PEG) is added to cause crystallization of the RuBisCO. It has been found that treatment of the resulting PEG supernatant first by acidification to remove other proteins, and then by addition of a strong base to remove phosphorylated sugars, allows the recycling of the PEG in the process. Moreover, it is found that the phosphorylated sugars are a valuable by-product, suitable for example as a carbon source for the culture of microorganisms.

4 Claims, No Drawings

METHOD FOR PREPARATION OF FRACTION I PROTEIN AND BY-PRODUCTS THEREOF

BACKGROUND OF THE INVENTION

1. Field of the Invention

The present invention relates to a method for preparing Fraction I protein from unpurified extracts of a variety of plant species by crystallization with polyethylene glycol, and more particularly to a method which provides for the removal of certain phosphorylated sugars from the polyethylene glycol solution and allows recycling of the solution.

2. Description of the Prior Art

Fraction I protein, the most abundant protein found in plants, has been identified as the enzyme ribulose 1,5-bisphosphate carboxylase (RuBisCO). Fraction I protein is widely distributed in nature and constitutes up to 50% of the water soluble protein contained in leaves and approximately 20% of the total plant protein. The amino acid composition of Fraction I protein is well balanced in terms of the essential and non-essential amino acids, comparing favorably with soybean, casein, and animal proteins. The amounts of the essential amino acids in Fraction I protein, with the exception of methionine, meet and often exceed most published human nutritional requirements.

For some years, it has been the goal of a number of scientific and industrial researchers to provide a large-scale method for recovering Fraction I protein from a variety of plant sources. Much work has been done, and substantial steps have been taken toward this goal. See, e.g., Paulsen and Lane (1966) Biochem. 52:2350–2357, describing a method for purifying spinach RuBisCO on a laboratory scale. Compare the more recent work described in U.S. Pat. Nos. 4,347,324 and 4,268,632 to Wildman et al., U.S. Pat. No. 3,340,676 to Bourque, and particularly U.S. Pat. Nos. 4,334,024 and 4,400,471 to Johal, the inventor herein.

While the methods taught in these references hold much promise, until the methods can be improved to provide for the efficient production of Fraction I protein on a commercial scale, their promise cannot be realized. For example, heretofore, recycling of polyethylene glycol (PEG) used to crystallize the RuBisCO has been difficult because of the presence of other substances released during fractionation of the plant material. Thus, it would be highly desirable to provide improved methods for the recovery of Fraction I protein from various plant sources on a large scale with relatively low costs, particularly methods which allow recycling of the PEG.

SUMMARY OF THE INVENTION

The present invention provides an economic method for the large-scale purification and crystallization of ribulose 1,5-bisphosphate carboxylase (RuBisCO) from a wide variety of plant species. It has been found that removal of certain phosphorylated sugars from a polyethylene glycol solution used to induce RuBisCO crystallization allows recycling of the PEG solution. Moreover, the phosphorylated sugars are a valuable by-product, useful for example as carbon sources in the culture of microorganisms.

According to the subject method, plant material is treated in a known manner to crystallize and remove the RuBisCO therefrom. The plant material is first comminuted in an aqueous solution to form a suspension. The suspension is then fractionated to release the RuBisCO into the suspension. The fractionating may be achieved either by heating the suspension or by chemical treatment. The RuBisCO is then removed from the suspension by crystallization induced by adding an effective amount of polyethylene glycol, usually in the presence of a low concentration of a salt such as magnesium chloride ($MgCl_2$).

It has been found by the inventor herein that certain phosphorylated sugars are also released into the PEG solution, and that the presence of these sugars inhibits the reuse or recycling of the PEG solution to treat fresh leaf preparations. The need to continually provide fresh PEG solution to treat the entire amount of processed leaf material is, of course, economically unattractive. By using the method of the present invention, the phosphorylated sugars can be removed from the spent PEG solution, enabling the reuse of the solution. Moreover, the recovered phosphorylated sugars are a valuable by-product which can be utilized as a carbon source for culture of microorganisms.

DESCRIPTION OF THE PREFERRED EMBODIMENT

According to the subject method, a portion of plant material, usually leaves, is comminuted and homogenized in an aqueous solution having a low concentration (typically 0.1M) of a reducing agent, such as sodium meta-bisulfite. The pH of the solution is not critical, typically being in the range from about 5.5 to about 8.5, usually being about 8.0. Conveniently, a buffer such as Tris-HCl buffer may be employed.

The crude leaf homogenate so obtained is then fractionated to release the RuBisCO by any conventional method for releasing proteins from plant material. Most simply, the homogenate can be exposed to heat, typically 37° C. to 40° C., for a period of approximately 10 minutes. Alternatively, fractionation of the homogenate may be chemically induced by any one of a variety of well known agents, such as dextrans, ammonium sulphate and various polymeric alcohols, including polyethylene glycol. It is preferred to induce fractionation using polyethylene glycol (PEG) since PEG (at a higher concentration) will act as a precipitant in crystallizing the RuBisCO, as will be described below. Sufficient PEG to bring the concentration to 8 weight-/volume percent is adequate.

After fractionation, the homogenate is filtered to remove the remaining membranes and organelles, and the residue is discarded. The filtrate is maintained at a cool temperature, preferably in the range from about 2° to 7° C.

Crystallization of the RuBisCO is effected by adding additional PEG, usually having a molecular weight in the range from about 5,000 to 7,000 daltons, preferably about 6,000 daltons. The final PEG concentration will be above about 8 weight/volume percent, preferably in the range from about 8 to 18 weight/volume percent, and more preferably in the range from about 11 to 16 weight/volume percent. The addition of magnesium chloride at a concentration in the range from about 0.01 to 0.04M, preferably from about 0.02 to 0.03M, following the addition of the PEG will enhance crystal formation and yield, although it is not necessary.

The RuBisCO crystals may be separated from the solution by any convenient method. The crystals may be allowed to settle by storing the solution at a temperature from about 4° C for about 2 to 10 hours, usually about 6 to 8 hours. Alternatively, the crystals may be separated by centrifugation. The pure RuBisCO crystals which are obtained may be collected, washed and stored, or lyophilized and stored. The crystal preparation so obtained has a carboxylase activity comparable to preparations made by other, more elaborate techniques.

Addition of PEG may be accomplished in two stages, although this is not necessary. It has been found that the two-stage addition facilitates the separation of the RuBisCO crystals, reducing the necessary centrifugation time and/or "g" value employed.

To this point, the method described is known and set forth in U.S. Pat. No. 4,400,471 to the inventor herein. Relevant portions of that patent are incorporated herein by reference. The novel aspects of the present invention concern the recycling of the supernatant which remains after the RuBisCO crystals have been separated. The supernatant is valuable since it retains substantially all of the PEG which has been added in earlier steps. However, it has been found that the PEG cannot simply be recycled for treatment of fresh leaf preparations. Rather, it has been found that the presence of certain phosphorylated sugars and other macromolecules inhibits the initiation of crystal formation when the spent PEG solution is recycled. The phosphorylated sugars appear to be a mixture of phosphorylated mono and disaccharides.

To remove the phosphorylated sugars, the pH of the PEG solution is raised to a value of at least 10, preferably at least 12, to cause the sugars to precipitate. Surprisingly, it has been found that substantially all of the sugars may be removed by such treatment, typically combined with centrifugation to remove the precipitate formed. Conveniently, the pH may be adjusted by the addition of a strong base, such as sodium hydroxide (NaOH). The pH of the solution should later be adjusted back into the range from about 5.5 to 8.0 prior to treatment of the leaf homogenate.

In addition to removal of the phosphorylated sugars, it is usually desirable to remove protein fractions other than Fraction I protein which have been released into the PEG solution. Conveniently, this may be accomplished by acidifying the PEG solution to a value above about 5.0, usually above about 3.0, until the protein fraction has been precipitated. Such proteins, referred to as Fraction II proteins, are less nutritionally attractive than the Fraction I proteins, although they have some value.

The following examples are offered by way of illustration, not by way of limitation.

EXPERIMENTAL

All percentages are by weight unless otherwise indicated. The following reagents were employed:
Buffer A —Tris, pH 7.6, 10mM $MgCl_2$, 100mM NaCl, 20mM $\beta$-mercaptoethanol
Buffer C—Tris, pH 8.0, 20mM Na-metabisulfite
Sabouraud's Media—dextrose (40g/1), peptone (10g/1), agar (15g/1), final pH 5.6
PEG—PEG 6000, Fisher Chemical Co., or J.T. Baker Chemical Co.

EXPERIMENT ONE

Destemmed alfalfa (58g) was added to Tris-HCl (150ml, pH 8.0). The leaf material was ground, and PEG (20%, 70ml) and 2M $MgCl_2$ (3.15ml) were added to the suspension. After centrifuging to remove the membranes and organelles, additional PEG (solid, 7.46g) was added to the supernatant, causing it to become cloudy. After refrigeration overnight (4° C), crystal formation was observed.

The crystals, which comprise the RuBisCO, were removed from the supernatant, washed with 16% peg solution and stored in 16% PEG. After two days, the crystals were centrifuged, and the pelleted crystals were dissolved in distilled water and lyophilized.

The supernatant (approximately 200ml) remaining after the crystals were removed was adjusted to pH 3.0 with conc. HCl. A precipitate was observed, the precipitate probably being protein. See U.S. Pat. No. 4,347,324 where Fraction II proteins are removed by acidification.

The precipitate was removed by centrifugation, and the supernatant treated with sufficient 10M NaOH to adjust to pH 12. Heavy precipitation was observed.

After storage overnight at room temperature, the last precipitate was removed by centrifugation, and the resulting supernatant adjusted to pH 8.0 with conc. HCl and stored for use in the next experiment. The PEG concentration in the supernatant was about 13%. Analysis revealed the precipitate to be a mixture of phosphorylated sugars.

EXPERIMENT TWO

Destemmed alfalfa (60g) was added to buffer C (175ml). The leaf material was ground, and the final supernatant (125ml) from Experiment One was added to the suspension. After centrifuging to remove the membranes and organelles, additional PEG (solid, 5.5g) was added to the supernatant, causing it to become cloudy. After refrigeration overnight (4° C), crystalline material was observed at the bottom of the beaker.

The crystals, which comprise the RuBisCO, were removed from the supernatant, washed in distilled water, and stored in 16% PEG.

The supernatant (approximately 290ml) remaining after the crystals were removed was adjusted to pH 3.0 with concentrated HCl. The precipitate was observed, and removed by centrifugation. The resulting pellet was discarded, and the supernatant adjusted to pH 12 with 10M NaOH. Additional precipitation was observed, which analysis showed to be phosphorylated sugars. The sugars were separated from the mixture by centrifugation, and the supernatant stored for reuse after adjusting the pH with concentrated HCl to pH 8.0.

EXPERIMENT THREE

The stemmed alfalfa (30g) was added to buffer C (100ml). The leaf material was ground, and the supernatant from Experiment Two (80ml) together with 2M $MgCl_2$ (2ml) was added. After centrifuging to remove the membranes and organelles, additional PEG (solid, 5g) was added to the supernatant, causing it to become cloudy. After refrigerating overnight (4° C) crystal formation was observed.

Crystals were removed from the solution by centrifugation, washed with PEG, and solubilized in distilled water. SDS-PAGE revealed the crystals to be substantially pure RuBisCO.

The supernatant (approximately 184ml) remaining after the RuBisCO crystals had been removed, was adjusted with the concentrated HCl to pH 3.0. The resulting precipitant was removed by centrifugation, and SDS-PAGE analysis showed the precipitate to be a mixture of proteins.

The supernatant resulting from the last centrifugation was adjusted to pH 12 with 10M NaOH, and a precipitate observed. The precipitate was removed by centrifugation, and the pellet washed with distilled water and stored. The remaining supernatant was adjusted to pH 8.2 with concentrated HCl.

EXPERIMENT FOUR

Destemmed alfalfa (115g) was added to a buffer (300ml) comprising Tris, pH 8.0, 0.1mM $Na_2EDTA$, β-mercaptoethanol. The leaf material was ground, and fresh PEG (20%, 140ml) added followed by 2mM $MgCl_2$ (6.3ml). After centrifugation, PEG (solid, 17g) was added and a precipitate obtained immediately. The crystals were amorphous and displayed a flat plate structure. After standing for two hours at room temperature, the mixture was centrifuged and the crystals removed. The crystals were washed with fresh PEG and the pellets solubilized in distilled water, and finally lyophilized.

The supernatant was adjusted to pH 3.0 with concentrated with HCl. The proteinaceous precipitant was removed by centrifugation, and the supernatant was adjusted to pH 12 with 10M NaOH. Heavy precipitation was observed, and the precipitant removed by centrifugation. The precipitant was saved for subsequent testing, and the supernatant discarded.

EXPERIMENT FIVE

Ryegrass (75g) was added to the same buffer (150ml) used in Experiment Four. After grinding, PEG solution from Experiment One was added (103ml). After centrifuging to remove waste material, PEG (solid, 11.2g) was added to the supernatant and precipitation observed. After refrigerated storage for about 15 hours, the precipitant at the bottom of the beaker appeared to be a mixture of crystal types. The crystal material was removed by centrifugation, washed, and stored. The supernatant was adjusted to pH 3.0 with concentrated HCl, and a precipitate observed. The precipitate was removed by centrifugation, and the supernatant adjusted to pH 12 with 10M NaOH. The resulting precipitate was separated by centrifugation, and the pellet washed with distilled water and stored. The supernatant was adjusted to pH 8.0 with concentrated HCl and stored at 4° C.

EXPERIMENT SIX

Tobacco leaves (120g) were added to buffer A, and the leaves were ground. The resulting mixture was brought to 10% PEG, and the waste material removed by centrifugation. Additional PEG (solid, 12.6g) was added to the supernatant, and a precipitate immediately observed. After standing for 1 hour at room temperature, the mixture was centrifuged and the resulting pellet removed.

The pellet was solubilized in buffer A, and again centrifuged. The pellet was discarded, and the supernatant dialyzed against buffer C in a collodion bag. Analysis revealed that the crystals present in the collodion bags were standard tobacco crystals, i.e., rhombic dodexahedrons.

EXPERIMENT SEVEN

The phosphorylated sugars obtained in the prior experiments were used as a carbon source for the culture of yeast. Dry yeast (Baker's yeast) was activated in warm distilled water in the presence of a small amount of sucrose. The growing yeast was then inoculated in the following growth media:

| Number | Medium | Results |
|---|---|---|
| 1 | Distilled water | No growth |
| 2 | Distilled water, sucrose, (200 g/l), | Good growth |
| 3 | Distilled water, sucrose, (200 g/l), sodium nitrate (15 g/l) | Growth slightly less than No. 2 |
| 4 | Distilled water, phosphorylated sugars* | Growth 70-80% of No. 2 |
| 5 | Distilled water, phosphorylated sugars* sodium nitrate (15 g/l) | Growth 60-70% of No. 2 |

*Obtained from Experiments 2 and 4, present at 200 g/l.

After incubating overnight, yeast from each of the growth media were plated onto Sabouraud's media on agarose plates under sterile conditions. The results are summarized in the above Table. Based on these results, the phosphorylated sugars obtained from the supernatants of the present invention appear to be suitable for use as carbon sources for the culture of microorganisms.

Although the foregoing invention has been described in some detail by way of illustration and example for purposes of clarity of understanding, it will be obvious that certain changes and modifications may be practiced within the scope of the appended claims.

What is claimed is:

1. An improved method for preparing ribulose 1, 5-bisphosphate carboxylase (RuBisCO) from plant material, said method comprising:
    (a) comminuting the plant material in an aqueous solution to form a suspension;
    (b) fractionating the suspension to release the RuBisCO from the comminuted plant material into the suspension;
    (c) adding a sufficient amount of polyethylene glycol (PEG) to the suspension so that crystals of RuBisCO are selectively formed;
    (d) separating the crystals from the suspension, leaving a supernatant; wherein the improvement comprises:
    (e) adjusting the pH of the supernatant to above 10 to cause precipitation of phosphorylated sugars;
    (f) separating the phosphorylated sugars from the supernatant; and
    (g) recycling the supernatant from step (f) to provide at least a portion of the PEG required in step (c) and repeating step (d) as often as is required to isolate substantially all of the RuBisCo crystals from the supernatant.

2. A method as in claim 1, wherein the supernatant is acidified to a pH below 5 prior to precipitation of the phosphorylated sugars in step (e), whereby a protein fraction other than RuBisCO is precipitated.

3. A method as in claim 1 wherein the pH is adjusted by the addition of a strong base in step (e).

4. A method as in claim 3, wherein the strong base is selected from the group consisting of NaOH, $NH_4OH$, $Ca_2$ and lime.

* * * * *